(12) United States Patent
Rieker et al.

(10) Patent No.: US 10,690,562 B2
(45) Date of Patent: Jun. 23, 2020

(54) APPARATUS AND METHODS FOR LOCATION AND SIZING OF TRACE GAS SOURCES

(71) Applicant: The Regents of the University of Colorado, a body corporate, Denver, CO (US)

(72) Inventors: Gregory B. Rieker, Boulder, CO (US); Kuldeep Prasad, Vienna, VA (US); Caroline B. Alden, Boulder, CO (US); Sean C. Coburn, Longmont, CO (US); Robert J. Wright, Boulder, CO (US)

(73) Assignees: The Regents of the University of Colorado, a body corporate, Denver, CO (US); Government of the United States of America, as represented by the Secretary of Commerce, Gaithersburg, MD (US)

( * ) Notice: Subject to any disclaimer, the term of this patent is extended or adjusted under 35 U.S.C. 154(b) by 0 days.

(21) Appl. No.: 16/343,363

(22) PCT Filed: Oct. 18, 2017

(86) PCT No.: PCT/US2017/057234
§ 371 (c)(1),
(2) Date: Apr. 18, 2019

(87) PCT Pub. No.: WO2018/075668
PCT Pub. Date: Apr. 26, 2018

(65) Prior Publication Data
US 2019/0265123 A1    Aug. 29, 2019

Related U.S. Application Data

(60) Provisional application No. 62/409,569, filed on Oct. 18, 2016.

(51) Int. Cl.
*G01M 3/16* (2006.01)
*G01N 33/00* (2006.01)
(Continued)

(52) U.S. Cl.
CPC ............... *G01M 3/16* (2013.01); *G01M 3/04* (2013.01); *G01M 3/38* (2013.01);
(Continued)

(58) Field of Classification Search
CPC ........... G01M 3/04; G01M 3/16; G01M 3/38; G01N 33/0027; G01N 33/0062;
(Continued)

(56) References Cited

U.S. PATENT DOCUMENTS 6,756,592 B1 * 6/2004 Smith ..................... G01J 3/457
250/338.5
2002/0169557 A1   11/2002 Gilbert et al.
(Continued)

OTHER PUBLICATIONS

International Search Report and Written Opinion of PCT/US2017/057234 dated Jan. 23, 2018, 13 pp.

*Primary Examiner* — Orlando Bousono
(74) *Attorney, Agent, or Firm* — Lathrop GPM LLP

(57) ABSTRACT

A system for detecting gas leaks and determining their location and size. A data gathering portion of the system utilizes a chosen geometrical configuration to collect path-integrated spectroscopic data over multiple paths around an area. A processing portion of the system applies a transport model together with meteorological data of the area to generate an influence function of possible leak locations on gas detector measurement paths, and applies an inversion model to the influence function, prior data, and the spectroscopic data to generate gas source size and location.

20 Claims, 11 Drawing Sheets

(51) Int. Cl.
  *G01W 1/00* (2006.01)
  *G01M 3/38* (2006.01)
  *G01M 3/04* (2006.01)
(52) U.S. Cl.
  CPC ..... *G01N 33/0027* (2013.01); *G01N 33/0062* (2013.01); *G01W 1/00* (2013.01)
(58) Field of Classification Search
  CPC .............. G01N 21/3504; G01N 21/39; G01N 2021/399; G01W 1/00; G01J 3/02; G01J 3/42
  See application file for complete search history.

(56) References Cited

U.S. PATENT DOCUMENTS

| | | | |
|---|---|---|---|
| 2004/0012787 A1* | 1/2004 | Galle | G01N 21/3504 356/437 |
| 2004/0021078 A1* | 2/2004 | Hagler | G01J 3/02 250/339.13 |
| 2004/0211900 A1* | 10/2004 | Johnson | G01J 3/108 250/338.5 |
| 2008/0195329 A1 | 8/2008 | Gilbert et al. | |
| 2009/0055103 A1 | 2/2009 | Gilbert et al. | |
| 2010/0198736 A1* | 8/2010 | Marino | G01N 21/3504 705/308 |
| 2011/0069309 A1 | 3/2011 | Newbury et al. | |
| 2011/0112772 A1* | 5/2011 | Yost | G01J 3/28 702/24 |
| 2011/0122397 A1* | 5/2011 | Wong | G01S 15/885 356/51 |
| 2011/0213554 A1* | 9/2011 | Archibald | G01V 9/007 702/6 |
| 2012/0153155 A1* | 6/2012 | Johnson | G01J 3/108 250/338.5 |
| 2014/0002639 A1 | 1/2014 | Cheben et al. | |
| 2014/0172323 A1* | 6/2014 | Marino | G01N 21/3504 702/24 |
| 2018/0284088 A1* | 10/2018 | Verbeck, IV | G01N 1/26 |

\* cited by examiner

APPARATUS AND METHODS FOR LOCATION AND SIZING OF TRACE GAS SOURCES

This invention was made with government support under grant numbers DE-AR0000539 and DE-FE0029168 awarded by the U.S. Department of Energy. The government has certain rights in the invention.

U.S. patent application Ser. No. 15/152,543, filed 11 May 2016, is incorporated herein by reference. Provisional application for patent No. 62/409,569, filed 18 Oct. 2016, is incorporated herein by reference.

BACKGROUND OF THE INVENTION

Field of the Invention

The present invention relates to apparatus and methods for detecting and locating gas leaks. In particular, the present invention relates to apparatus and methods of accounting for prior data on background emissions (i.e., ambient or baseline concentrations upon which signals from monitored leaks are imposed) to better geographically characterize the leak.

Discussion of Related Art

Current open-path techniques that are capable of measuring methane leaks over long paths include diode laser-based absorption systems, LIDAR systems, and FTIR-based systems. Mobile FTIR systems suffer from low wavelength resolution (large instrument distortion), and have thus far only demonstrated ~5-10% measurement uncertainty for trace GHGs, which is far too great to detect, locate, and size methane leaks at kilometer scale standoff distances.

Diode laser-based systems and LIDAR systems focus on measurements of a few wavelengths around a single absorption feature of methane (or a wavelength sweep over 1-2 features). High precision, long-term stability, and accuracy is difficult due to turbulence-induced laser intensity fluctuations and interference from overlapping absorption of other molecules that are not included in spectral fits. Even techniques which rely on detection of phase shifts induced by absorption features (instead of direct absorption) must account for phase shift induced by any absorbing component in the beam path and neighboring absorption features.

Sparse wavelength laser systems also do not typically measure other species, temperature, pressure, or water vapor. A simultaneous measurement of water vapor, temperature, and pressure is desirable for correcting measured methane mole fractions to dry-air mole fractions, to account for time varying dilution effects of water vapor change on the apparent concentration of methane. In addition, water vapor, temperature and pressure influence methane absorption feature shape, which is important when fitting the absorption features to accurately extract the methane mole fraction for calibration-free operation.

Many previous methane studies near oil and gas operations were performed with commercial cavity-ringdown laser spectrometers (CRDS) either fixed, or mounted on vehicles and aircraft. These spectrometers enable very high sensitivity with short measurement times, but require periodic calibration, and are expensive. For specific leak detection, the sensors either require an operator (pilot or driver) or a network of multiple expensive sensors and common calibration.

Several other types of low-cost in-situ sensors for methane exist. Some focus on making flux measurements because they are not stable over long periods of time. Others lack the measurement precision needed to identify smaller leaks or need to be calibrated often and corrected for effects of temperature, pressure, humidity, or other interfering species (possibly requiring regular access to the well pad). Other in-situ sensors with lower cost than CRDS sensors still require either an operator to get spatial information or multiple sensors. Using multiple sensors requires inter-calibration and inter-comparability between the various sensors to correct for background fluctuations in methane with a remote background sensor or to compare methane concentration between sites. In a distributed system, each sensor may require power and communication.

FIGS. 1A-1C (Prior Art) illustrate the operation of a dual comb spectroscopy (DCS) system that is useful in the data gathering portion of the present invention. 1A (Prior Art) is a schematic block diagram illustrating the process of passing two frequency combs through a gas and detecting the resulting light. The two frequency combs (e.g. near infrared light) have slightly different tooth spacing that are combined as source light that passes through a gas. FIG. 1B (Prior Art) shows the two frequency combs after the light passes through the gas so that some light frequencies have been absorbed by the gas. FIG. 1C (Prior Art) illustrates the resulting heterodyne interference signals of the combs at, e.g., radiofrequency (RF) frequencies.

DCS as the spectrometer overcomes limitations of single or sparse wavelength absorption or LIDAR approaches. Namely, DCS enables accurate correction of baseline laser intensity of frequency combs (302, 304) and simultaneous measurement of hydrocarbons such as $CH_4$, $^{13}CH_4$, ethane, acetylene, and the like as well as other species such as water and conditions such as temperature, pressure, and the like. Therefore, the spectrometer provides interference-free, true dry-air mole fractions that account for variable water vapor dilution. Without instrument distortion, e.g., of line shape, and a near perfect wavelength axis, the spectroscopic absorption technique provided by the gas spectrometer monitor is drift-free and requires no calibration. Compared with single point measurements that might be deployed on a tower or a mobile platform (e.g., aircraft, vehicle, and the like), the spectrometer monitor requires no operator involvement and can interrogate multiple locations simultaneously.

A need remains in the art for apparatus and methods for improved detection and geographical characterization of gas leaks including apparatus and methods for accounting for background emissions.

SUMMARY OF THE INVENTION

It is an object of the present invention to provide apparatus and methods for improved detection and geographical characterization (such as size and location) of gas leaks including apparatus and methods for accounting for background emissions.

A low cost dual comb spectrometer design uses the method of deploying a line of sight, broadband, laser absorption sensor to locate and size trace gas leaks. An embodiment of the present invention includes an open path spectrometer gas detector combined with a transport model and an inversion model to size and locate gas leaks.

A system according to the present invention determines the location and size of a gas source within an area by providing a spectrometer gas detector, collecting path-integrated spectroscopic data over multiple open paths around the area with the detector, collecting meteorological data related to the area, applying a transport model together with meteorological data to generate source-receptor relationships (where source is a potential emission location/time and receptor is a measurement location/time) for potential source locations on gas detector measurement paths, and using the source-receptor relationships with an inversion model and spectroscopic data to generate gas source size(s) and location(s). The spectrometer might be based on a dual comb spectrometer. In a preferred embodiment, the transport model is a large eddy simulation or other computational fluid dynamics model, a Lagrangian particle dispersion model, or a Gaussian plume or puff model. The system might employ a number of reflectors, such as retroreflectors arrayed within or around the area, or a mobile reflector, for example on a UAV. The meteorological data might be measured onsite or provided by a simulation model of the area. Some embodiments use Kalman filtering, a Bayesian statistical inversion, or least-squares fitting to estimate emissions.

The system might include a telescope for transmitting laser beams and receiving the reflected beams, and a gimbal for orienting the telescope to scan the area.

Apparatus and methods of geometrically characterizing a gas source within an area according to the present invention include the steps of providing a spectrometer gas detector, collecting path-integrated spectroscopic data over gas detector measurement paths around the area with the detector, collecting meteorological data related to the area, collecting prior data related to existing gas emission in the area, applying a transport model together with meteorological data to generate source-receptor relationships describing influence of emissions from potential source locations on gas detector measurement paths, and applying an inversion model based on source-receptor relationships, spectroscopic data, and prior data to geographically characterize a gas source. The geographical characterization may locate leaks, or size them, or both. The meteorological data might be measured or simulated. The prior data may include uncertainty.

Various geometries may be used for the data gathering portion of the system, including a Fenceline configuration where reflectors encapsulate the area, an Orthogonal Beam Sampling configuration with reflectors upwind and downwind from a suspected leak, or a Clustering configuration using a plurality of gas spectrometer monitors. The Clustering configuration allows simultaneous processing of data from the monitors and informing prior data for individual monitors based on data from the other monitors.

Some embodiments include bootstrapping model uncertainties in order to produce an empirical distribution of source strength for points within the area, to determine likelihood of a leak.

BRIEF DESCRIPTION OF THE DRAWINGS

FIG. 1B (Prior Art) shows the two frequency combs after the light passes through the gas. FIG. 1C (Prior Art) illustrates the resulting heterodyne interference signals.

DETAILED DESCRIPTION OF THE INVENTION

Figure 1A:
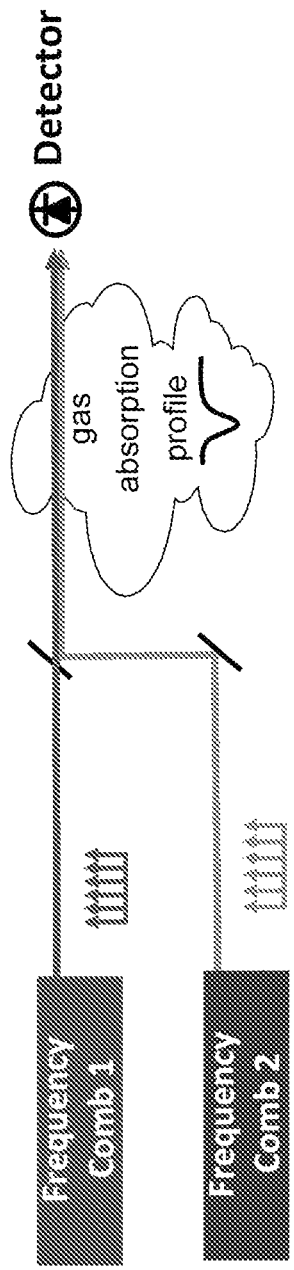
FIGS. 1A-1C (Prior Art) illustrate the operation of a dual comb spectroscopy (DCS) system that is useful in the data gathering portion of the present invention. 1A (Prior Art) is a schematic block diagram illustrating the process of passing two frequency combs through a gas and detecting the resulting light.
Figure 1B:
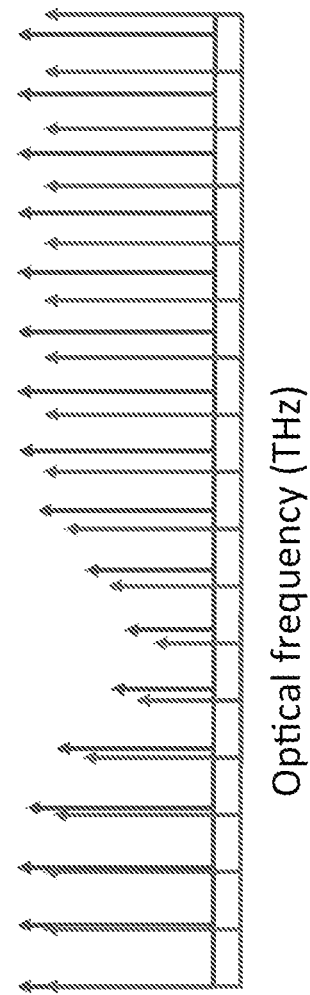
Figure 1C:
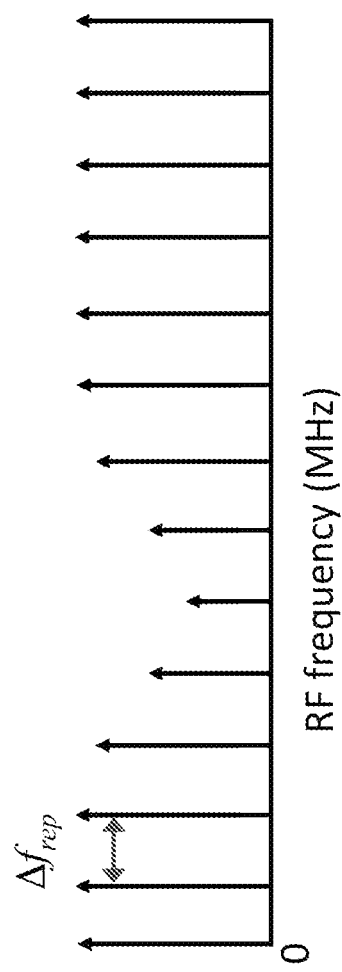

FIGS. 1A-1C (Prior Art) illustrate the operation of a dual comb spectroscopy (DCS) system that is useful in the gas detection portion of the present invention 1A (Prior Art) is a schematic block diagram illustrating the process of passing two frequency combs (e.g. near infrared light) having slightly different tooth spacings through a gas and detecting the resulting light. FIG. 1B shows the two frequency combs after the light passes through the gas, so that some light frequencies have been absorbed by the gas. FIG. 1C illustrates the resulting heterodyne interference signals at the detector, for example at radio (RF) frequencies.

DCS overcomes the key limitations of single or sparse wavelength absorption or LIDAR approaches: it enables accurate correction of the baseline laser intensity, and simultaneous measurement of $CH_4$, $^{13}CH_4$, $H_2O$, other species (such as ethane and propane), temperature, and pressure. It therefore reports interference-free, true dry-air mole fractions that account for variable water vapor dilution. With no instrument distortion (of lineshape) and a near perfect wavelength axis, the technique is also drift-free and requires no calibration. Compared with single point measurements that might be deployed on a tower or mobile platforms (aircraft or cars), this solution requires no operator involvement and can interrogate multiple locations simultaneously.

Figure 2:
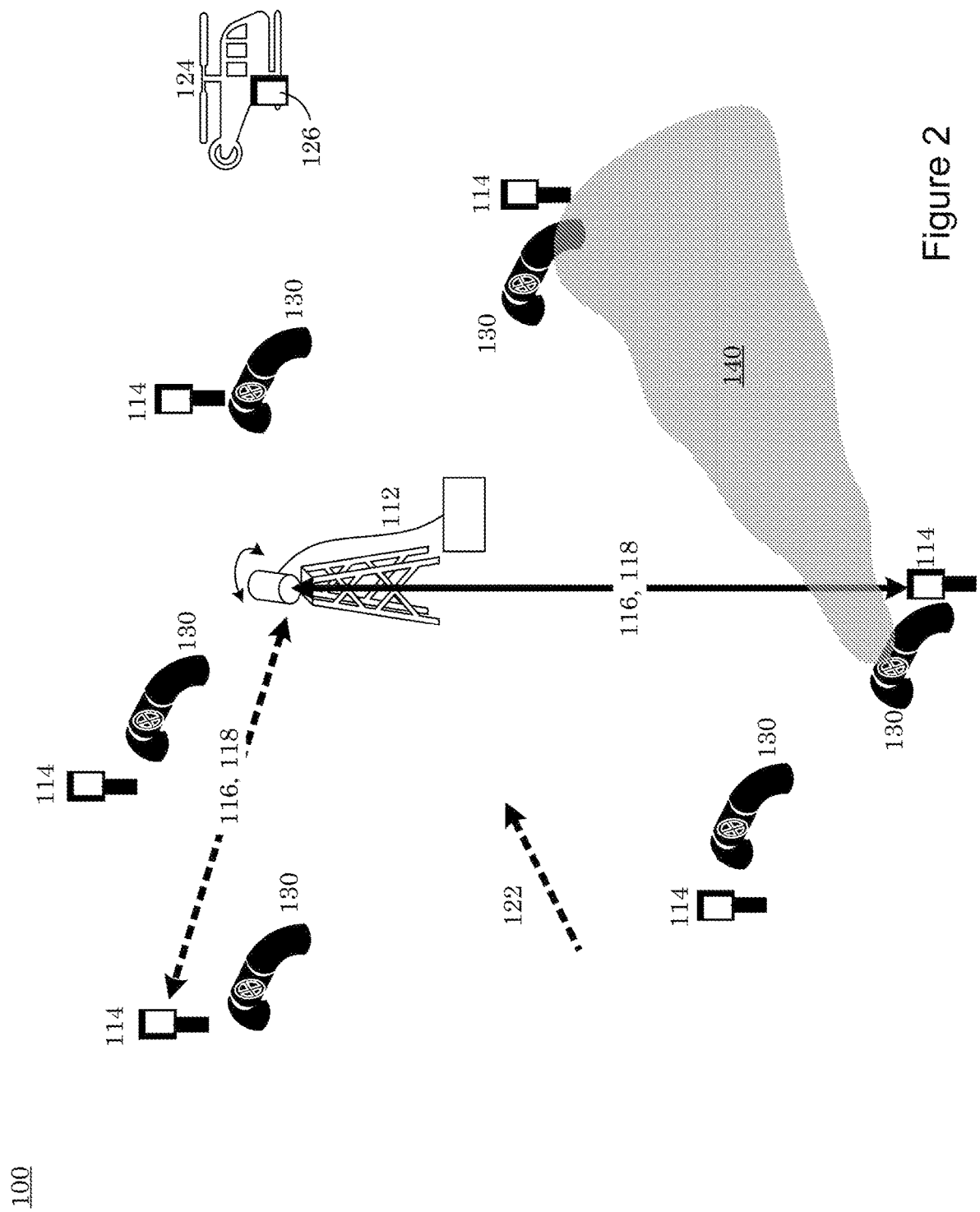
FIG. 2 is a diagram illustrating an embodiment of the data gathering portion of the present invention using a hub-and-spoke geometry.

FIG. 2 is a diagram illustrating an embodiment of the data gathering portion 200 of the present invention using a hub-and-spoke geometry. This geometry is described in more detail in U.S. patent application Ser. No. 15/152,543 (incorporated herein by reference). The present invention improves the previous system by incorporating background subtraction to the processing accomplished in processor 410 (see FIGS. 3 and 4). The open path hub-and-spoke system of FIG. 2 includes a central spectrometer/detector unit 112 and several reflectors 114 arrayed over an area to allow unit 112 to transmit and receive light in a variety of directions to detect plumes from gas leaks 140 from a number of wells 130. Unit 112 scans the area with laser beams 116 over long open paths and detects the light reflected from reflectors 114. Data is generally collected over a period of hours, days or weeks under various weather conditions.

A processor 404 (see FIGS. 3 and 4) combines spectrometer data 350 with concurrent meteorological data 340 (such as the direction and speed of wind 122) of the area, as well as prior information (including in some embodiments uncertainty) 360, to determine the size and/or location of any gas leaks. For example, processor 404 combines observation processing with a transport model and inversion techniques to locate and size the leaks.

In some embodiments, reflectors 114 are retroreflectors that reflect the light directly back to the spectrometer/detector unit 112. Retroreflectors provide a high degree of pointing flexibility (the beams from a large array of incoming angles are re-directed back the direction they came in), and thus alignment is automatic as long as the beam can track the retro-reflector.

Reflectors 114 might be located on well platforms or risers, towers, trees, fences, etc. Alternative reflectors may be used, including other fixed reflectors and even environmental reflectors such as buildings. In some embodiments, a UAV 124 with a reflector 126 periodically flies a fixed path around the area and beams 116 are reflected off of reflector 126 in various directions covering the area containing wells 130.

Figure 3:
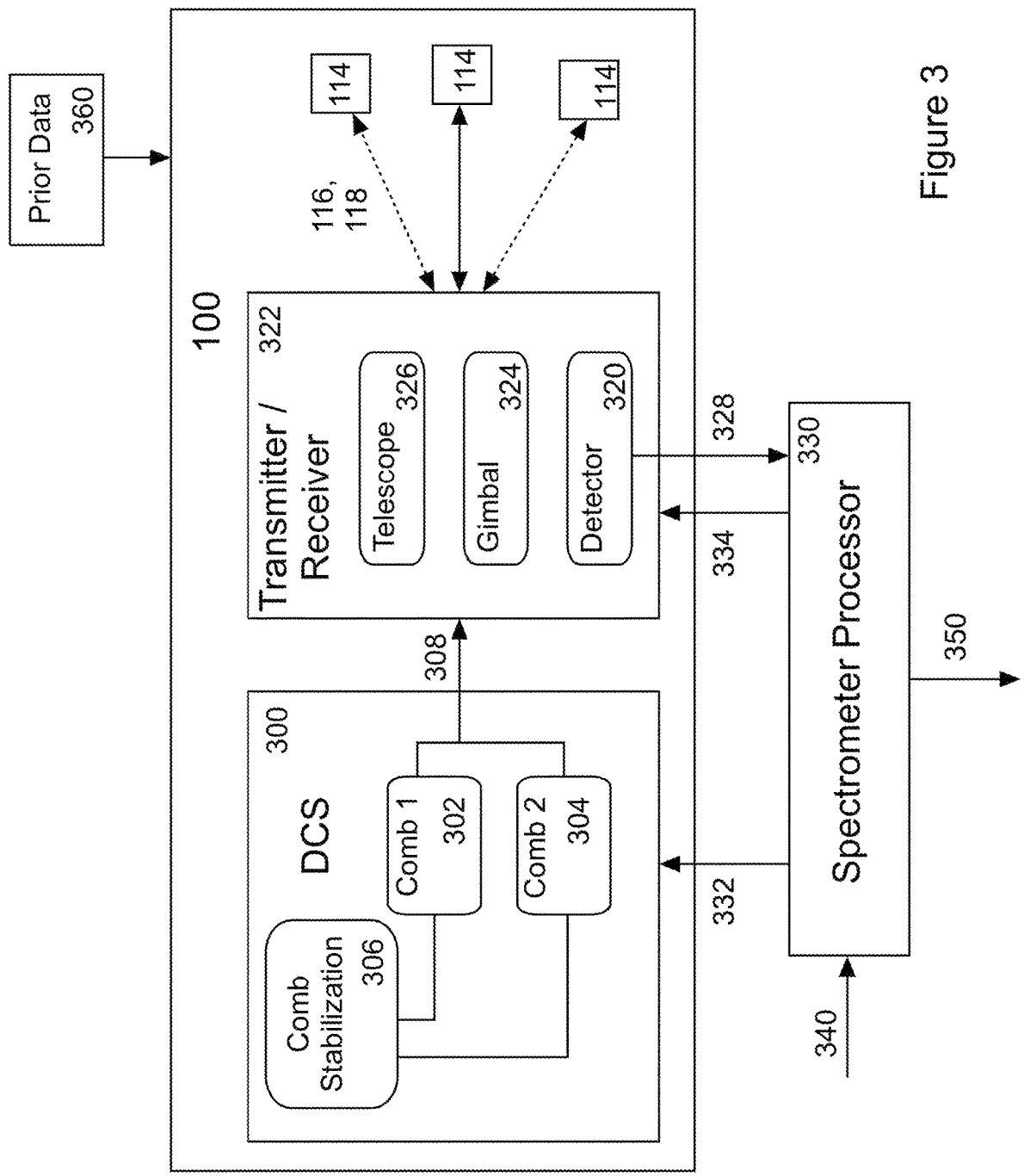
FIG. 3 is a block diagram illustrating an embodiment of the data gathering process and spectrometer processing according to the present invention.

One particularly useful embodiment includes a dual comb spectrometer (DCS) unit 300 (See FIG. 3). Since DCS 300 is compatible with fiber optic transmission, it is possible to monitor the perimeter of large facilities using several paths serviced by a single spectrometer via fiber optics. The same is true of multiple centralized towers separated by many kilometers. The same is also true of multiple beams originating from a single location. A single DCS spectrometer can supply light via optical fiber to multiple origin points to reduce system cost.

The frequency comb spectrometer provides low cost and high performance. The frequency combs can be assembled from telecommunications fiber and telecom components that have a selected mean time between failures of more than 200,000 hours. An optics package of the frequency comb spectrometer can be, e.g., 0.7 liters. Frequency comb control electronics can include a field programmable gate array (FPGA) and can be similarly small.

In a preferred embodiment, a central, high-performance spectrometer/detector unit 112 sends light 116 sequentially or simultaneously over different open paths to retroreflectors 114. The measured absorption spectra are fit to determine methane concentration enhancements. Atmospheric transport modeling and inversion techniques are used to interpret the measured enhancement into methane leak size and location. The 3 ppb sensitivity of spectrometer/detector unit 112 enables detection of small leaks over a range of heights and downwind distances, thus enabling flexible location of retroreflectors 114. Accurate, sensitive, calibration- and drift-free measurements of methane have been demonstrated over a 2 km open-air path. Another preferred embodiment (called clustering) comprises a series of proximally located (neighboring) hub-and-spoke systems from which data is combined into a single or a series of inversions for leak location and size.

FIG. 3 is a block diagram illustrating the data gathering process according to the present invention. The system transmits DCS beams 116 via transmitter/receiver 322 toward reflectors 114 and detects the reflected beams 118. Spectrometer processor 330 combines data 328 from the detector 320 with meteorological data 340 to generate spectrometer processing output 350. Meteorological data is used to model atmospheric transport of gas after emission as leaks 140.

Prior data 360 may be used to help determine the data gathering geometry chosen.

DCS unit 300 includes two comb units 302 and 304, as well as circuitry 306 to stabilize the generated comb combination 308 and/or to electronically post-correct the spectroscopic signal 328. Combs 308 are provided to transmitter/receiver unit 322 including telescope 326 for transmitting and receiving light beams 116, 118, gimbal 324 to scan beams 116 over the area, and detector 320 to detect the reflected beams 118 from reflectors 114 and provide data 328 to processor 330.

Processor 330 provides control signals 332, 334 to DCS unit 300 and transmitter/receiver unit 322. It also receives detector data 328 from detector 320 and meteorological data 340. Spectrometer processor 330 outputs spectrometer data 350 comprising, for example, the path integrated trace gas concentration values along each source 116 and reflected 118 beams.

Meteorological data 340 might comprise local measurements of wind 122, as well as temperature, humidity, etc. Alternatively, it could be determined from regional measurements or meteorological simulations of the area, such as the Weather Research and Forecasting Model (WRF). Or a combination of these methods may be used.

Figure 4A:
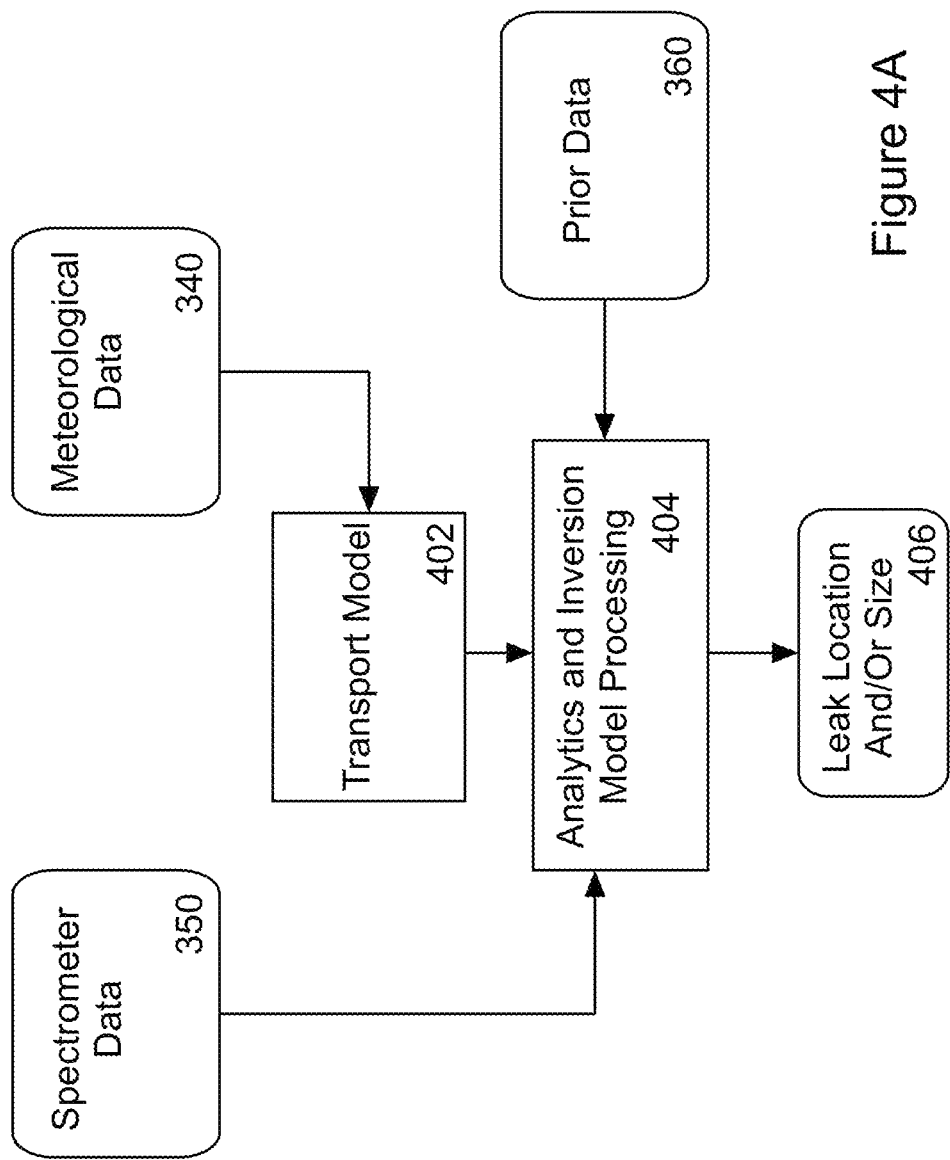
FIG. 4A is a flow diagram illustrating a general embodiment of the signal processing portion of the present invention.

FIG. 4A is a flow diagram illustrating a general embodiment of the signal processing portion of the present invention. Meteorological data 340 are provided to a transport model 402. Transport model 402 is used to create source-receptor relationships 424 (where source is a potential emission location/time and receptor is a measurement location/time) that are passed together with spectrometer data 350 and prior data 360 to the analytics and inversion model processor 404 that computes the leak location and size 406.

Figure 4B:
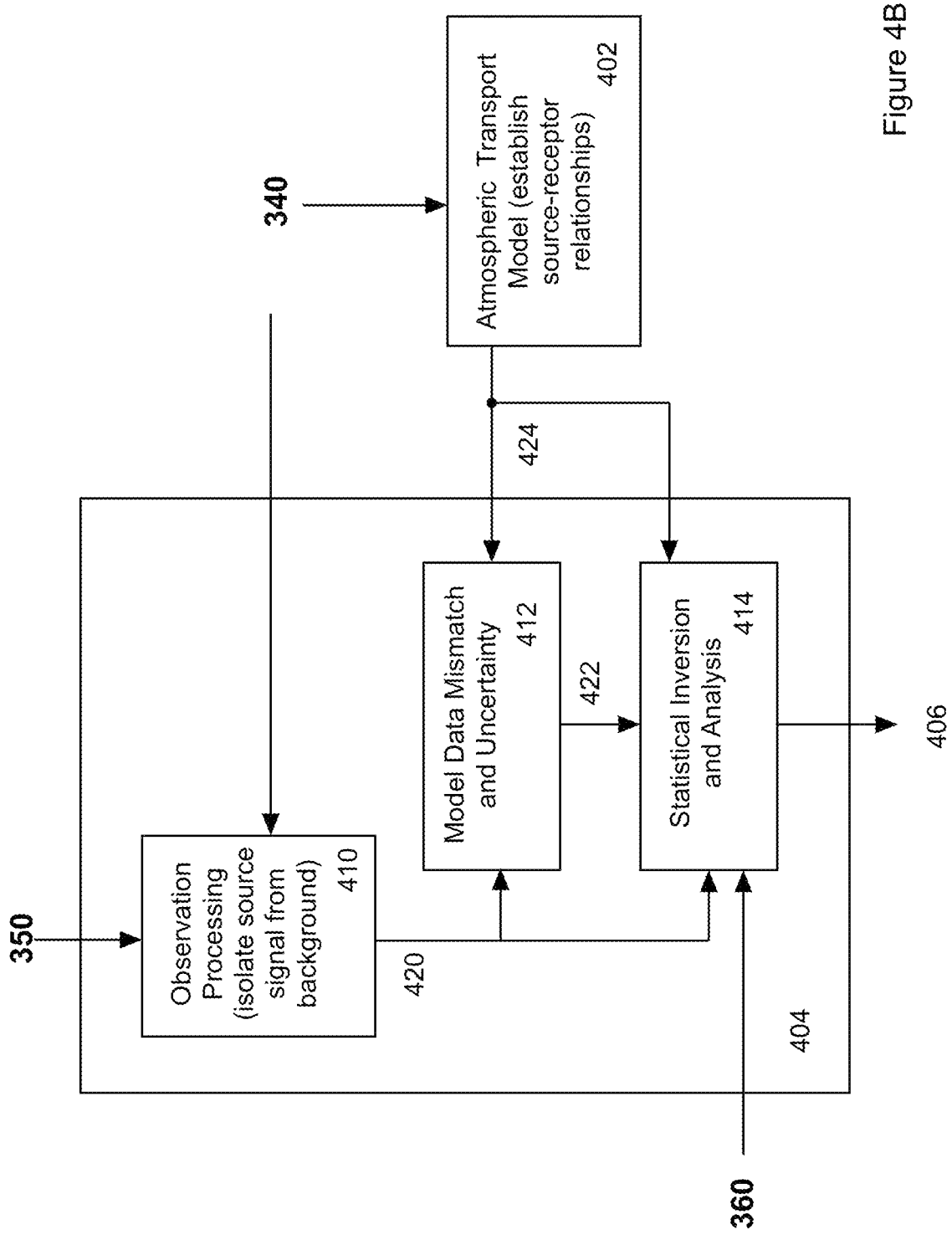
FIG. 4B is a flow diagram illustrating a specific embodiment of the preferred signal processing portion of the present invention.

FIG. 4B is a flow diagram illustrating one preferred embodiment of analytics and inversion model processor 404. Spectrometer data 350 is provided as an input to inversion model 404 and is processed in block 410, observation processing. Block 410 can isolate the signal from the background to generate observation data 420. The particular processing accomplished by block 410 will vary with the chosen geometry used for data gathering, as shown in later figures. Observation data 420 is compared to source-receptor relationships 424 by model data mismatch and uncertainty block 412, wherein observed and source-receptor data along with associated uncertainties for each data point are together analyzed to generate output 422 which describes the differences between observed and source-receptor data. Block 414 accomplishes statistical inversion and analysis based on prior data 360, observation data 420, mismatch output 422, and source-receptor relationships 424.

Certain embodiments of the transport model 402 can incorporate the local topography (elevation, large buildings, vegetation, etc.) and local measurements of wind, temperature, and pressure for the inversion technique. Meteorological data 340 is provided as an input to the transport model 402. Meteorological data 340 can include local measurements of wind 122, temperature, humidity, and the like. Meteorological data 340 can be measured or simulated for area 110, e.g., from models such as the Weather Research and Forecasting (WRF) Model.

Prior data 360 can include prior (a priori) knowledge of potential leak locations. This knowledge can include information that can reasonably be gathered using surveys of the area(s) to be studied, particularly using satellite imagery or industry activity data. Prior knowledge of likely leak rates can also come from "bottom-up" or inventory analyses of where leaks are likely to be located and what their emission rates are likely to be. In the most basic application of our methodology, however, only the general (precision to within ~5 m×5 m) locations of facilities and components is necessary.

Prior data 360 can used to inform the locations and orientations of the transmitter/receiver 322, and the retroreflectors 114 and laser beams 116, 118 as shown in FIG. 3. The number of retroreflectors deployed in a given field of observation can depend on the number of leak locations to be monitored. The number of locations to be monitored can, for example, equal the number of priors. The number of retroreflectors deployed in a given field of observation can depend on the desired spatiotemporal resolution of leak detection and attribution or desired precision of quantification.

Prior data 360 can used as an input to the analytics and inversion model processing 404 shown in FIG. 4A. For example, if the inversion methodology employs least-squares fitting or a Bayesian inversion, the prior knowledge of potential leak locations determines the locations at which the model estimates emission rates.

Prior data 360 can used as input to the atmospheric transport model 402. Prior data 360 can be used as input to post-processing steps 414 following atmospheric transport modeling. In both cases, the prior data is used to simulate the individual relationships between each potential source location (prior) and each receptor location (for example, each segment of each laser beam).

Figure 5:
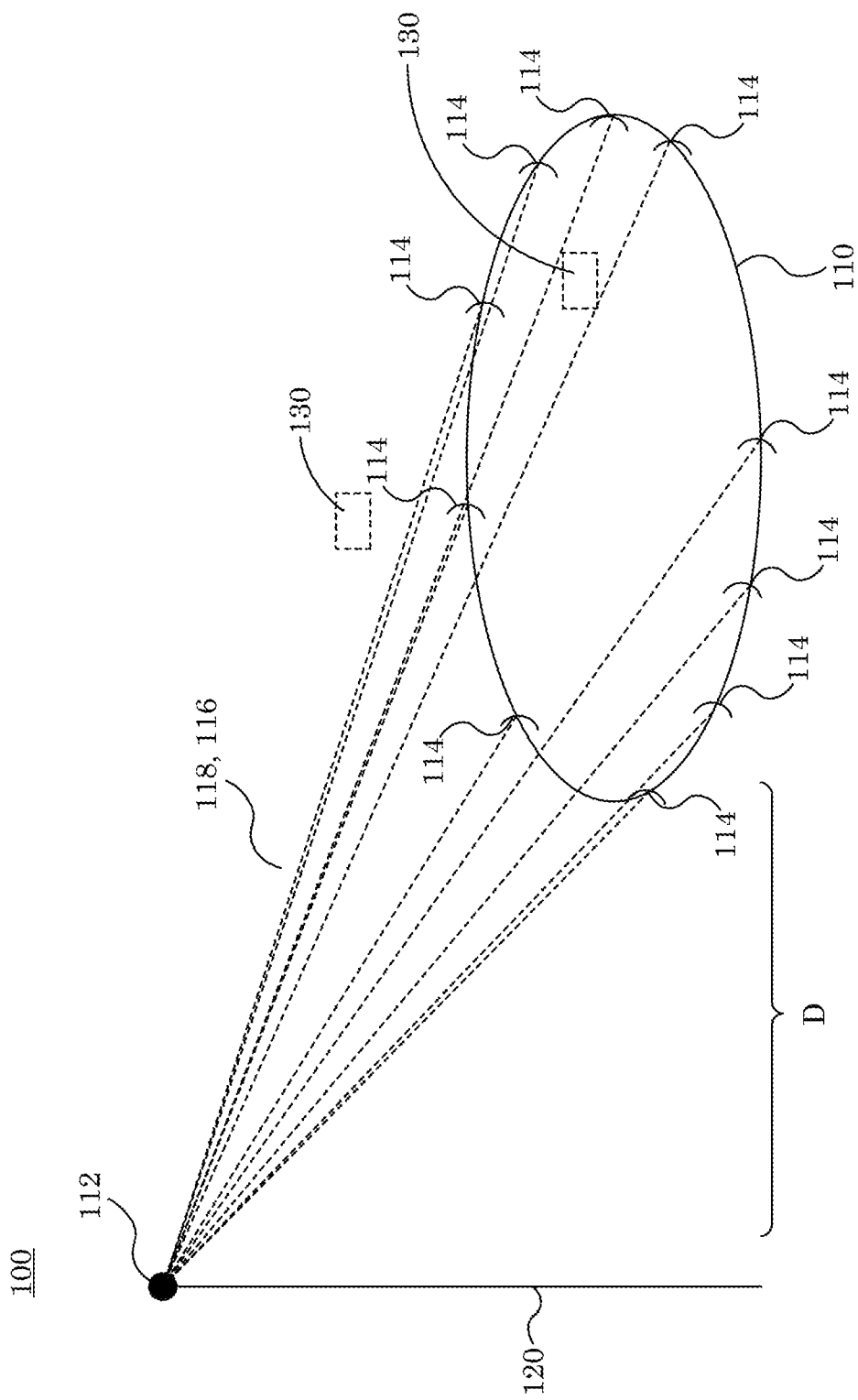
FIG. 5 is a schematic diagram of a data gathering system according to the present invention utilizing fence line geometry.
Figure 6:
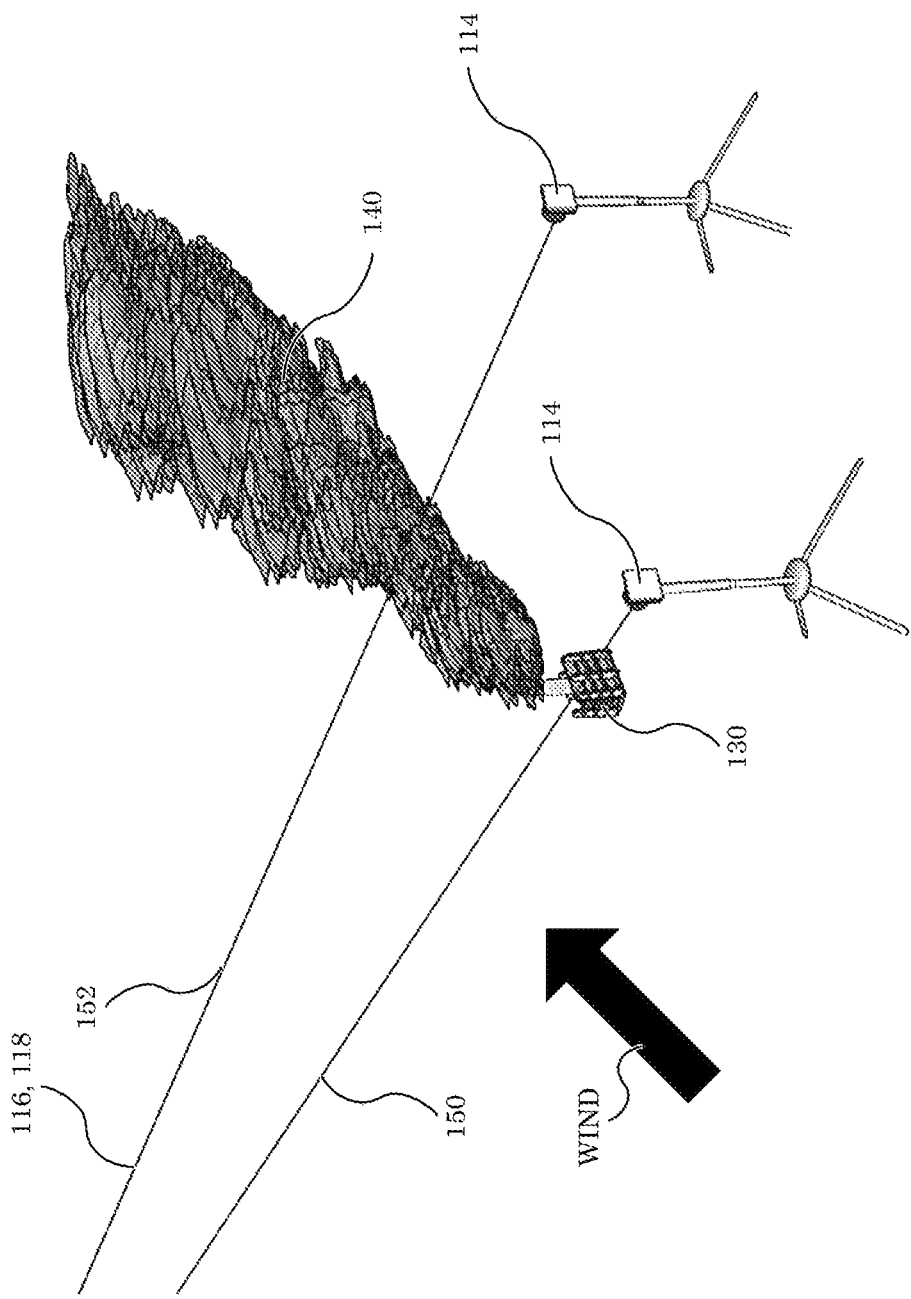
FIG. 6 is a schematic diagram of a data gathering system according to the present invention utilizing orthogonal beam sampling.
Figure 7:
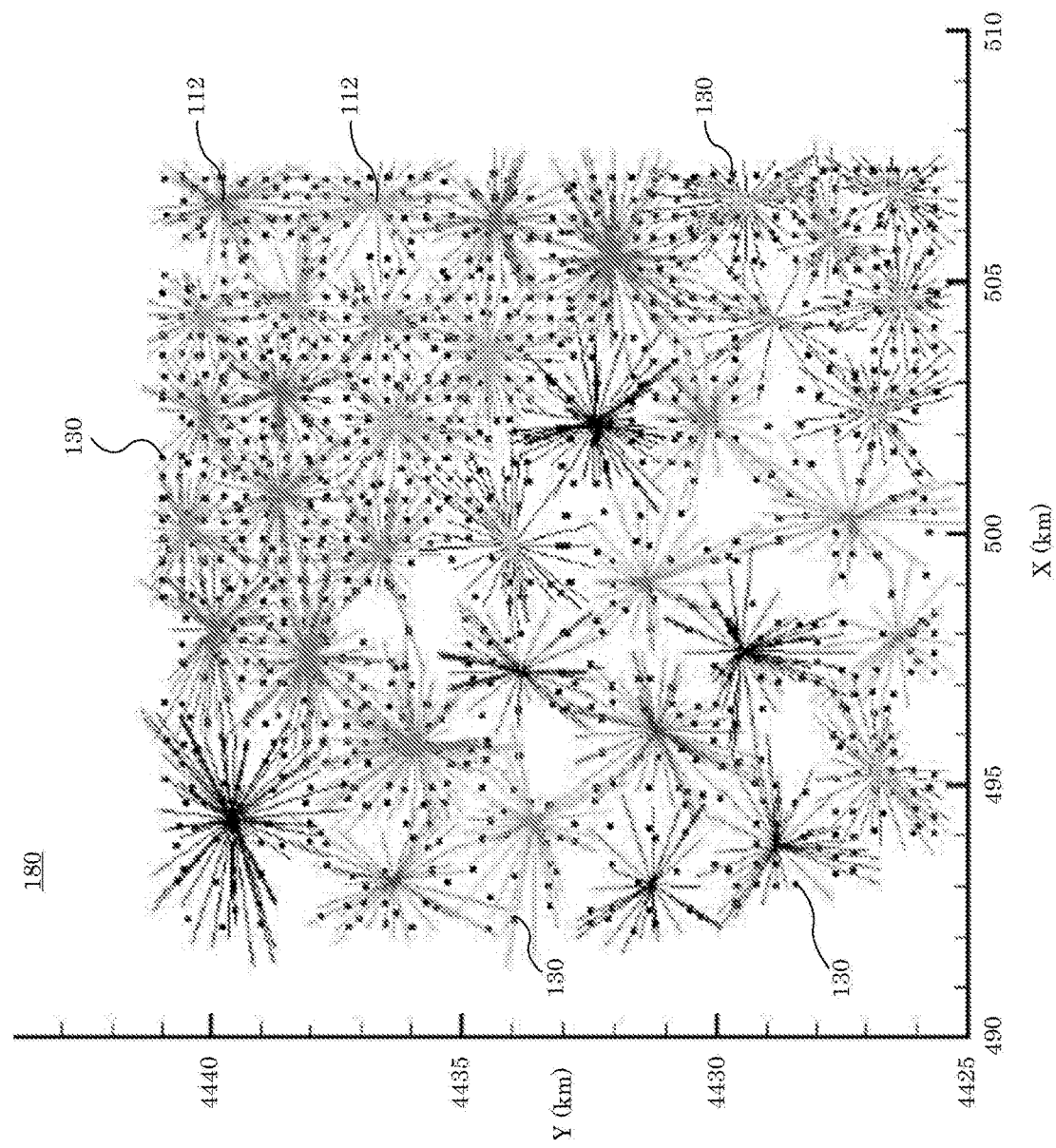
FIG. 7 is a top schematic view of a data gathering system according to the present invention utilizing clustering.
Figure 8:
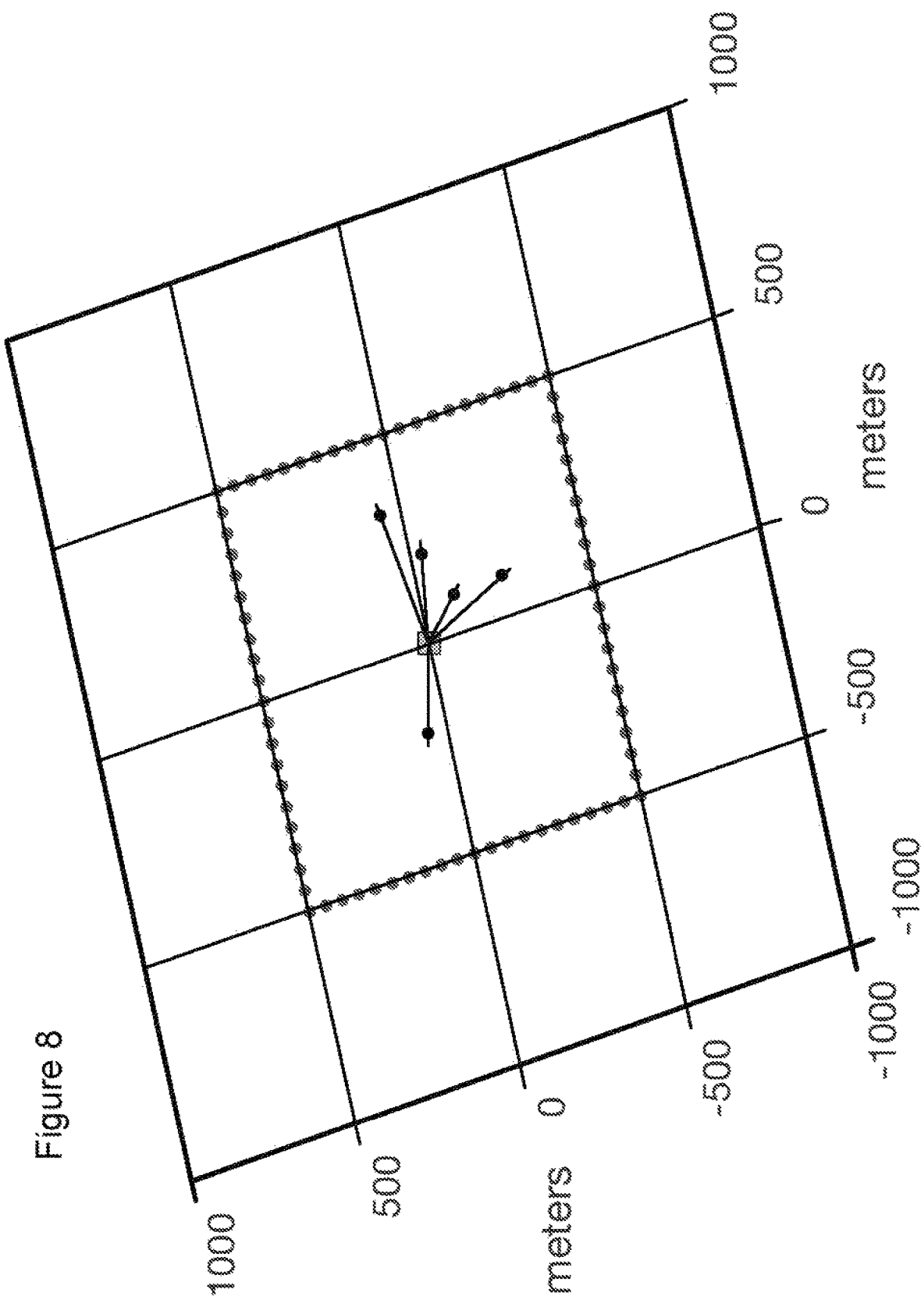
FIG. 8 is a top schematic view of a data gathering system using background subtraction and boundary constraints to reduce influence of leaks outside the inversion domain.

FIGS. 5 through 8 show examples of data gathering geometries. FIG. 5 shows an example of a data gathering geometry called "Fenceline Monitoring." FIG. 6 shows orthogonal beam sampling data gathering geometry. FIG. 7 shows a clustering data gathering geometry. FIG. 8 shows a data gathering geometry utilizing background subtraction and boundary constraints.

FIG. 5 is a schematic diagram of a system according to the present invention utilizing fence line geometry. Leak detection, attribution and quantification under the "Fenceline Monitoring" geometry can proceed in several ways.

The processing accomplished by observation block 410 for fence line monitoring can be accomplished by using beams 116, 118 that are upwind of the facility during any given meteorological condition(s) to constrain the background or concentration of the trace gas of interest in the inflowing "ambient" air. In this case, the beams 116, 118 that are downwind of a source would record an enhancement in the trace gas above background, and that signal would be isolatable by the processing in block 410 for possible use in the inversion block 404 to determine the likely location and strength of any leak(s) detected.

The processing accomplished by block 410 for fence line monitoring can be accomplished using beams 116, 118 to monitor for increases or other changes in the trace gas concentration that emerge as differences between beams 116, 118. The baseline, background or ambient trace gas concentration can, in this way, be identified and signals arising from potential leaks isolated and used in an inversion to determine the likely location and strength of any leak(s) detected.

Spectrometer 112 is disposed outside of area 110 or within area 110. It should be appreciated that retroreflectors 114 provide a fence line that encapsulates area 110 in a beam umbrella that includes open-path beams of source light 116. Accordingly, any gas that flows into or out of area 110 can be subjected to source 116 and reflected 118 light. Since retroreflectors 114 reflect source light 116 as reflected light 118 to spectrometer 112, the detector of spectrometer 112 can detect a difference in source light 116 and reflected light 118 due to absorption of source light 116 or reflected light 118 by the gas. It is contemplated that 110 can include gas source 130, wherein gas source 130 is an origin of gas 140. Moreover, wind 122 can be a meteorological factor that affects gas 140 inside or outside of area 110.

In an embodiment, spectrometer 112 can be disposed on a pole 120 or other structure for elevation of spectrometer 112 above a ground plane of area 110. With reference to FIG. 3, spectrometer 112 on pole 120 can be distance D from proximate retroreflector 114. Distance D can be selected based on various characteristics of spectrometer 112, area 110, meteorological conditions, and the like. In an embodiment, spectrometer 112 can also be disposed on any other structure or the ground and at any other height, and spectrometer 112 can also be located inside of area 110.

In some embodiments, retroreflectors 114 reflect source light 116 as reflected light 118 directly back to spectrometer 112. Retroreflectors 114 can provide a high degree of pointing flexibility, e.g., beams from a large array of incoming angles can be re-directed back the direction from which they came. As such, alignment of retroreflectors 114 with respect to spectrometer 112 can be automatic, and spectrometer 112 can be configured to track retroreflector 114.

Retroreflectors 114 can be located on a well platform, riser, tower, tree, fence, and the like. Alternative reflectors to retroreflectors 114 can be used, including other fixed reflectors or environmental reflectors such as buildings. In some embodiments, and unmanned aerial vehicle (UAV) 212 with reflector 126 periodically flies a path around area 110 and source light 116 is reflected as reflected light 118 off of reflector 126 in various directions covering area 110 containing gas source 130 (e.g., a well, well pad, and the like).

FIG. 6 is a schematic diagram of a system according to the present invention utilizing orthogonal beam sampling. The chosen geometry for data gathering is that of orthogonal (upwind-downwind) beam sampling. Leak detection, attribution and quantification under the "Orthogonal Beam Monitoring" geometry can proceed in several ways. Orthogonal beam sampling refers to a general case in which trace gas emissions from a given region (e.g., area 130 in FIG. 6) can be isolated from background or ambient trace gas conditions by sampling air inflow both upwind of and downwind of that region. In the processing or inversion steps, the enhancement above background determined by differencing the upwind and downwind measured concentrations can yield a signal that can be used as an input to the inversion.

Here, a pair of retroreflectors 114 are disposed relative to gas source 130 such that gas source 130 is interposed between retroreflectors 114. In this manner, source light 116 and reflected light 118 occur on both sides of gas source 130 so that gas 140 travels orthogonally or at any angle through downwind beam 152 (that includes second source light 116 and second reflected light 118), but plume of gas 140 is absent from (does not intersect) the upwind beam 150 (that includes first source light 116 and first reflected light 118). Accordingly, downwind beam 152 records different spectroscopic data from upwind beam 150. Moreover, second source light 116 in downwind beam 152 has different spectroscopic data and then second reflected light 118 in downwind beam 152.

FIG. 7 is a top view of a schematic diagram of a system according to the present invention utilizing clustering. For this geometry, processing of information and estimating leaks can be arrived at either by processing of data from individual spectrometers or by simultaneous processing of data from all spectrometers to arrive at a quasi-"global"

solution whereby the background for any spectrometer within the core of a cluster can be informed by surrounding spectrometers.

The area in which clustering takes place may include one or a plurality of gas sources 130; a plurality of gas spectrometer monitors 100 disposed as cluster 180 in which adjacent spectrometers 112 monitor gas 140 for gas sources 130 across area 110.

In an embodiment, with reference to FIG. 4B, processed spectrometer data 350 is further processed by block 410 to generate observation data 420 which is then utilized by analytics and inversion model processor 404 to determine the location and/or size of gas source 130. According to an embodiment, processor 404 combines observation data 420 with a transport model 402 and inversion techniques 414 to locate and size gas 140 from gas source 130.

In an embodiment, spectrometer 112 sends source light 116 sequentially over different long open paths to retroreflectors 114. The measured absorption spectra from reflected light 118 are fit to determine a concentration enhancement of gas 140 (e.g., a hydrocarbon such as methane). Inversion techniques can be used to interpret the measured enhancement into methane leak size and location of gas source 130. A sensitivity of spectrometer 112 provides detection of small leaks of gas 140 over a range of heights and downwind distances so that a location of retroreflectors 114 is flexible. Measurement of gas 140 from gas source 130 is accurate, sensitive, calibration and drift-free.

In an embodiment, with reference to FIGS. 3, 4A, and 4B, gas spectrometer monitor 100 includes processor 330 in communication with spectrometer 112. Here, spectrometer 112 communicates source light 116 via transmitter/receiver 322 to retroreflectors 114, receives reflected light 118 from retroreflectors 114, and detects reflected light 118. Process 330 combines spectroscopic data 328 from detector 320 with meteorological data 340 (such as a direction and speed of wind 122) of area 110 to provide processed spectrometer data 350 which is further processed to observation data 420 which is then utilized by analytics and inversion model processor 404 to determine the location of gas source 130. Meteorological data 340 is involved in modeling plume shape or path of gas 140 from gas source 130.

Spectrometer 112 includes light source 300. An exemplary light source 300 is a dual comb source that includes first frequency comb 302 and second frequency comb 304 as shown in FIG. 3. Operation of light source 300 for dual comb spectroscopy (DCS) provides detection of gas 140 from gas source 130, as shown in FIGS. 1A, 1B, and 1C (Prior Art).

Spectrometer 112 includes comb units (302, 304) and stabilizer circuitry 306 to stabilize generated comb combination 308 or to electronically post-correct the spectroscopic data 328. Combs 308 are provided to transmitter/receiver unit 322 including telescope 326 for transmitting source light 116 and receiving reflected light 118, gimbal 324 to scan beams of source light 116 over area 110, and detector 320 to detect reflected light 118 from retroreflectors 114 and provide spectroscopic data 328 to processor 330.

Processor 330 provides control signals (332, 334) to light source 300 and transmitter/receiver unit 322. Process 330 also receives spectroscopic data 328 from detector 320 and meteorological data 340. Processor 330 outputs 350 the path integrated trace gas concentrations values along each source 116 and reflected 118 beams.

FIG. 8 is a top schematic view of a data gathering system using background subtraction and boundary constraints to reduce influence of leaks outside the inversion domain. The chosen geometry for data gathering can use background subtraction and boundary constraints to reduce influence of leaks outside the inversion domain. The analytics and inversion processing 404 in this geometry uses a set of priors 360 that includes possible leak locations and also includes a series of points located around the perimeter of the observed domain. The priors that are around the perimeter are not located at potential leak sites; rather, they are positioned at the boundary so as to capture the influence of emissions that may be upwind of and in the near-field of the domain.

The chosen geometry for data gathering can be to process all beam concentrations in the inversion as one (as opposed to discrete sets of beams in Orthogonal sampling): wherein individual sectors of the domain are not isolated using upwind and downwind beams, but instead all measurements used on all beams are used in one inversion. In this case, a "global" (domain-wide) background is estimated, and this can be performed in a number of ways, including but not limited to finding the lowest beam concentration, and using perimeter grid cell "priors" (as described above) to capture the influence of nearfield outside leaks.

Figure 9:
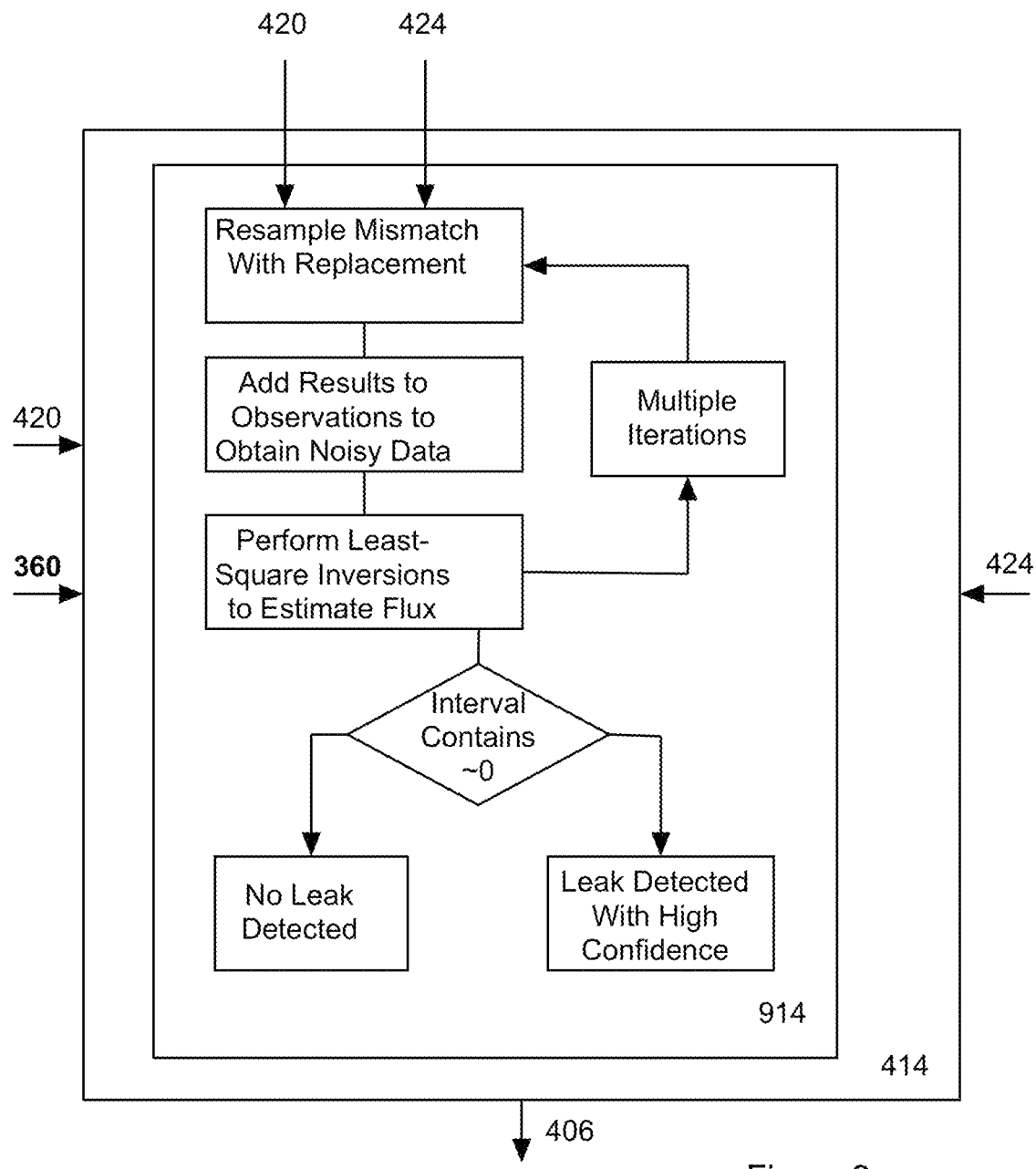
FIG. 9 is a flow diagram illustrating bootstrapping.
Figure 10:
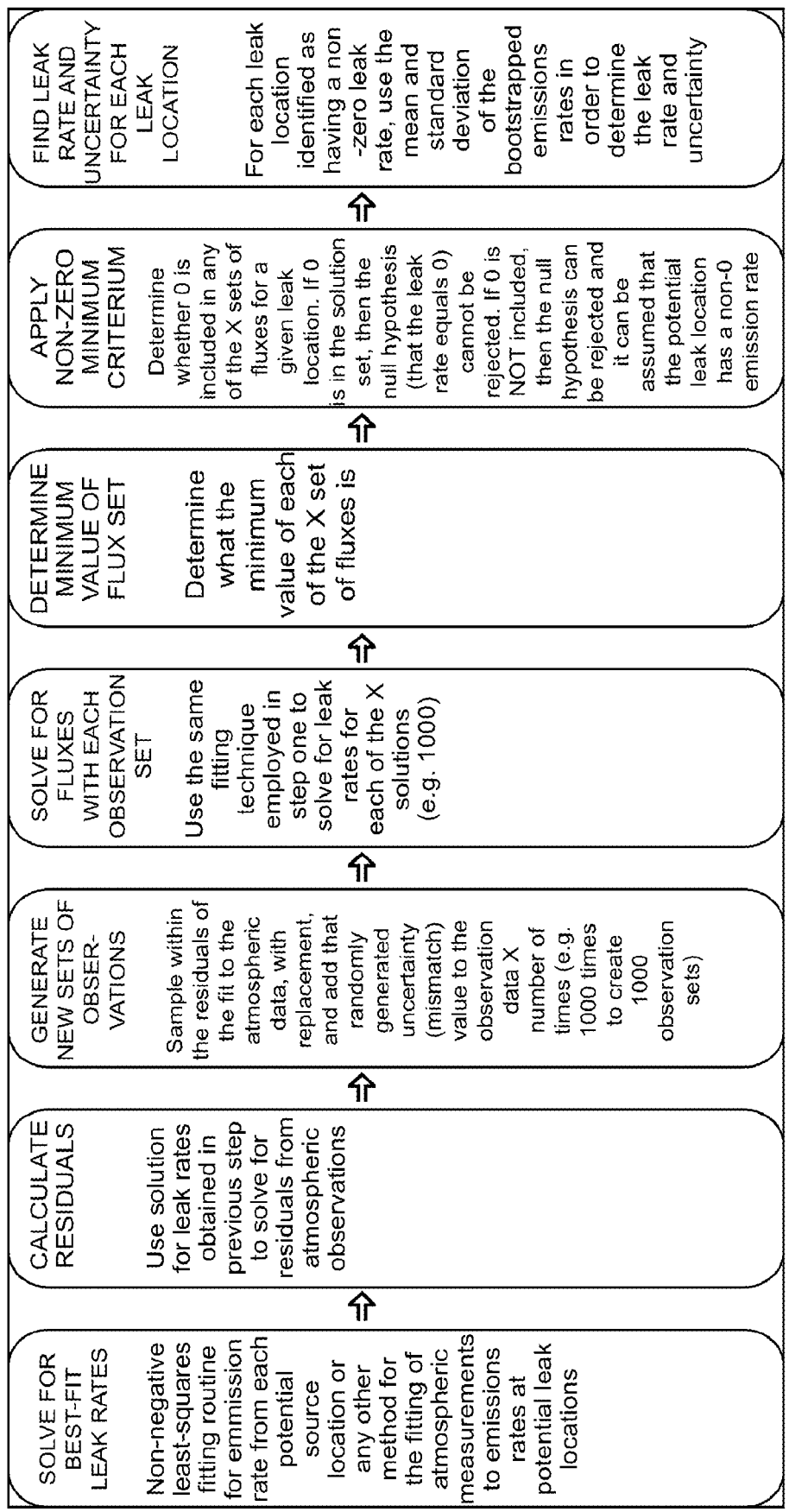
FIG. 10 is a flow diagram illustrating bootstrapping.

FIGS. 9 and 10 are flow diagrams illustrating the bootstrapping process as applied to the present invention. Applying bootstrapping to observation data 420 includes a statistical method for accurately locating one or more point sources within an area using distributed measurements of methane concentration and an atmospheric transport model. The method can be coupled with an atmospheric observing system that provides quasi-continuous monitoring of facilities. The source-attribution method uses any fitting technique (for example, non-negative least-squares fitting technique) to solve for methane flux at a series of prior locations, given a set of atmospheric observations and knowledge of atmospheric transport.

Applying zero minimum elimination to observation data 420 includes bootstrapping of model uncertainties in order to produce an empirical distribution of source strength for a given well site. Specifically, the empirical distribution is obtained by performing multiple atmospheric inversions using a set of resampled atmospheric measurements.

The method establishes a criterion by which well sites or facilities are identified as having non-zero methane emissions based on examination of the minimum value of an ensemble of inversions. A potential leak site is positively identified as a source of methane to the atmosphere if the empirical cumulative distribution of likely source strengths does not include zero flux. Similarly, a facility is identified as not leaking if the empirical cumulative distribution of likely source strengths does include zero. By defining a specific null value for each potential leak, this approach reduces the incidence of false positive leak identification. In an embodiment, the process includes measuring an atmospheric concentration of gas 140 from gas source 130 along the open-path beams.

While the exemplary preferred embodiments of the present invention are described herein with particularity, those skilled in the art will appreciate various changes, additions, and applications other than those specifically mentioned, which are within the spirit of this invention. For example, this technique could be used to locate and determine the flux of any gas source. The technique could be extended to look for other trace gasses besides methane to, for example, look for chemical leaks in industrial facilities or to, for example, look for $CO_2$ leaks at a carbon sequestration site. Other extensions could determine emissions from industrial sites, agricultural sites, animal-raising operations, or chemical and biological weapons releases.

The invention claimed is:

1. A method for characterizing at least one gas source located in a geographical area, comprising:
using a transport model with meteorological data related to the geographical area to generate source-receptor relationships that describe influence of emissions from the at least one gas source on path-integrated spectroscopic data collected for open paths around the geographical area; and
determining emissions information for the at least one gas source by applying an inversion model to the source-receptor relationships, the path-integrated spectroscopic data, and prior data indicating one or more known or potential gas sources in the geographical area.

2. The method of claim 1, wherein the emissions information includes one or more of a presence, a location, and a size of the at least one gas source.

3. The method of claim 1, wherein the prior data includes locations of one or more facilities or components that are the one or more potential gas sources.

4. The method of claim 1, wherein the prior data includes uncertainty.

5. The method of claim 1, wherein:
the method further comprises isolating a source signal in the path-integrated spectroscopic data from background to obtain observation data; and
said applying the inversion model includes applying the inversion model to the observation data, the prior data, the source-receptor relationships, and uncertainties related to interpretation of the observation data.

6. The method of claim 5, wherein the uncertainties related to interpretation of the observation data include model-data mismatch uncertainties.

7. The method of claim 1, wherein said using the transport model further uses the prior data to generate the source-receptor relationships.

8. The method of claim 1, wherein said applying the inversion model employs a least-squares fitting technique.

9. The method of claim 1, wherein said applying the inversion model employs a Bayesian inversion technique.

10. The method of claim 1, further comprising measuring the meteorological data related to the geographical area.

11. The method of claim 1, further comprising simulating the geographical area to obtain the meteorological data related to the geographical area.

12. The method of claim 1, further comprising collecting the path-integrated spectroscopic data by:
transmitting light from a spectrometer unit to each of a plurality of retroreflectors arrayed over the geographical area; and
detecting, with the spectrometer unit, the transmitted light after reflecting off said each of the plurality of retroreflectors;
wherein each of the open paths is defined by a location of the spectrometer unit and a location of a corresponding one of the plurality of retroreflectors.

13. The method of claim 12, further comprising placing the plurality of retroreflectors in a fenceline configuration such that the retroreflectors surround the geographical area.

14. The method of claim 12, further comprising placing the plurality of retroreflectors in an orthogonal beam sampling configuration such that at least one of the plurality of retroreflectors is located upwind from the at least one gas source and at least one other of the plurality of retroreflectors is located downwind from the at least one gas source.

15. The method of claim 12, wherein said transmitting includes transmitting light sequentially from the spectrometer unit to each of the plurality of retroreflectors.

16. The method of claim 1, wherein:
the spectrometer unit is one of a plurality of spectrometer units arranged in a cluster configuration; and
the method further comprises:
repeating, for each spectrometer unit of the plurality of spectrometer units, said using and said determining to obtain one or both of emissions information and an ambient concentration for said each spectrometer unit, and
using one or both of the emissions information and the ambient concentration from one of the plurality of spectrometer units as prior data for processing the path-integrated spectroscopic data collected by one or more other spectrometer units of the plurality of spectrometer units.

17. The method of claim 1, further comprising bootstrapping model uncertainties to produce an empirical distribution of source strengths for a plurality of potential source locations, wherein the empirical distribution is used to determine likelihood of a non-zero emission rate at each of the plurality of potential source locations.

18. An apparatus for characterizing at least one gas source located in a geographical area, comprising:
a spectrometer unit configured to transmit light to each of a plurality of retroreflectors arrayed over the geographical area, and to detect the transmitted light after reflecting off said each of the plurality of retroreflectors;
a spectrometer processor configured to process an output of the spectrometer unit to generate path-integrated spectroscopic data for an open path between the spectrometer unit and said each of the plurality of retroreflectors; and
a processor configured to:
use a transport model with meteorological data related to the geographical area to generate source-receptor relationships that describe influence of emissions from the at least one gas source on the path-integrated spectroscopic data, and
determine emissions information for the at least one gas source by applying an inversion model to the source-receptor relationships, the path-integrated spectroscopic data, and prior data indicating one or more known or potential gas sources in the geographical area.

19. The apparatus of claim 18, wherein the spectrometer unit is a dual comb spectrometer.

20. The apparatus of claim 18, wherein the processor is further configured to:
isolate a source signal in the path-integrated spectroscopic data from background to obtain observation data, and
apply the inversion model to the observation data, the prior data, the source-receptor relationships, and uncertainties related to interpretation of the observation data.

* * * * *